United States Patent
D'Alessandro et al.

(10) Patent No.: US 8,753,833 B2
(45) Date of Patent: Jun. 17, 2014

(54) COPOLYMER ASSAY

(75) Inventors: Josephine S. D'Alessandro, Marblehead, MA (US); Takashi Kei Kishimoto, Lexington, MA (US); Aileen Healy, Medford, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 776 days.

(21) Appl. No.: 12/665,794

(22) PCT Filed: Jun. 19, 2008

(86) PCT No.: PCT/US2008/067508
§ 371 (c)(1),
(2), (4) Date: Nov. 15, 2010

(87) PCT Pub. No.: WO2008/157697
PCT Pub. Date: Dec. 24, 2008

(65) Prior Publication Data
US 2011/0053203 A1    Mar. 3, 2011

Related U.S. Application Data

(60) Provisional application No. 60/945,488, filed on Jun. 21, 2007.

(51) Int. Cl.
*C12Q 1/02* (2006.01)
*A61K 45/00* (2006.01)

(52) U.S. Cl.
USPC .......................................... 435/29; 424/280.1

(58) Field of Classification Search
USPC .......................................... 435/29; 424/280.1
See application file for complete search history.

(56) References Cited

U.S. PATENT DOCUMENTS

| | | | |
|---|---|---|---|
| 3,849,550 A | 11/1974 | Teitelbaum et al. | |
| 4,683,202 A | 7/1987 | Mullis | |
| 6,251,639 B1 | 6/2001 | Kurn | |
| 6,692,918 B2 | 2/2004 | Kurn | |
| 7,862,807 B2 | 1/2011 | Goodman et al. | |
| 2004/0091956 A1 | 5/2004 | Bejan et al. | |
| 2006/0154862 A1* | 7/2006 | Ray et al. | 514/12 |

FOREIGN PATENT DOCUMENTS

| | | |
|---|---|---|
| EP | 0414533 | 2/1991 |
| WO | 95/31990 | 11/1995 |
| WO | 03/048735 | 6/2003 |
| WO | 2004/043995 | 5/2004 |
| WO | 2006/050122 | 5/2006 |
| WO | 2007/022193 | 2/2007 |
| WO | 2007/047202 | 4/2007 |

OTHER PUBLICATIONS

Li et al. Glatiramer acetate blocks the activation of THP-1 cells by interferon-γ. European Journal of Pharmacology 342 (1998) 303-310.*
Li et al. (Glatiramer acetate blocks the activation of THP-1 cells by interferon-gamma. European Journal of Pharmacology 342 (1998) 303-310).*
Li Q Q et al., "Glatiramar acetate inhibition of tumor necrosis factor-alpha-induced RANTES expression and release from U-251 MG human astrcytic cells," Journal of Neurochemistry 77:1208-1217 (2001).
Milo R et al., "Additive effects of copolymer-1 and interferon beta-1b on the immune response to myelin basic protein," Journal of Neuroimmunology 61:185-193 (1995).
Farina C et al., "Treatment of multiple sclerosis with Copaxone (COP): Elispot assay detects COP-induced interleukin-4 and interferon-gamma response in blood cells," Brain: A Journal of Neurology APR 124:705-719 (2001).
Ben Abdelaziz Halim et al., "Inhibition of TNF-alpha production in THP-1 macrophages by glatiramer acetate does not alter their susceptibility to infection by Listeria monocytogenes and does not impair the efficacy of ampicillin or moxifloxacin against intracellular bacteria," Journal of Antimicrobial Chemotherapy 54:288-289 (2004).
Klein et al. "IFN-Inducible Protein 10/CXC Chemokine Ligand 10-Independent Induction of Experimental Autoimmune Encephalomyelitis", J Immunol, 172:550-559, 2004.
Teitelbaum et al., "Suppression of experimental allergic encephalomyelitis by a synthetic polypeptide" Eur. J. Immunol. 1:242-248, 1971.
Jian Hong et al., Gene expression profiling of relevant biomarkers for treatment evaluation in multiple sclerosis, Journal of Neuroimmunology,2004,152:126-139, Dec. 31, 2004.

* cited by examiner

*Primary Examiner* — Karen Cochrane Carlson
*Assistant Examiner* — Natalie Moss
(74) *Attorney, Agent, or Firm* — Fish & Richardson P.C.

(57) ABSTRACT

The present invention provides methods and compositions for evaluating one or more properties of an amino acid copolymer.

11 Claims, 1 Drawing Sheet

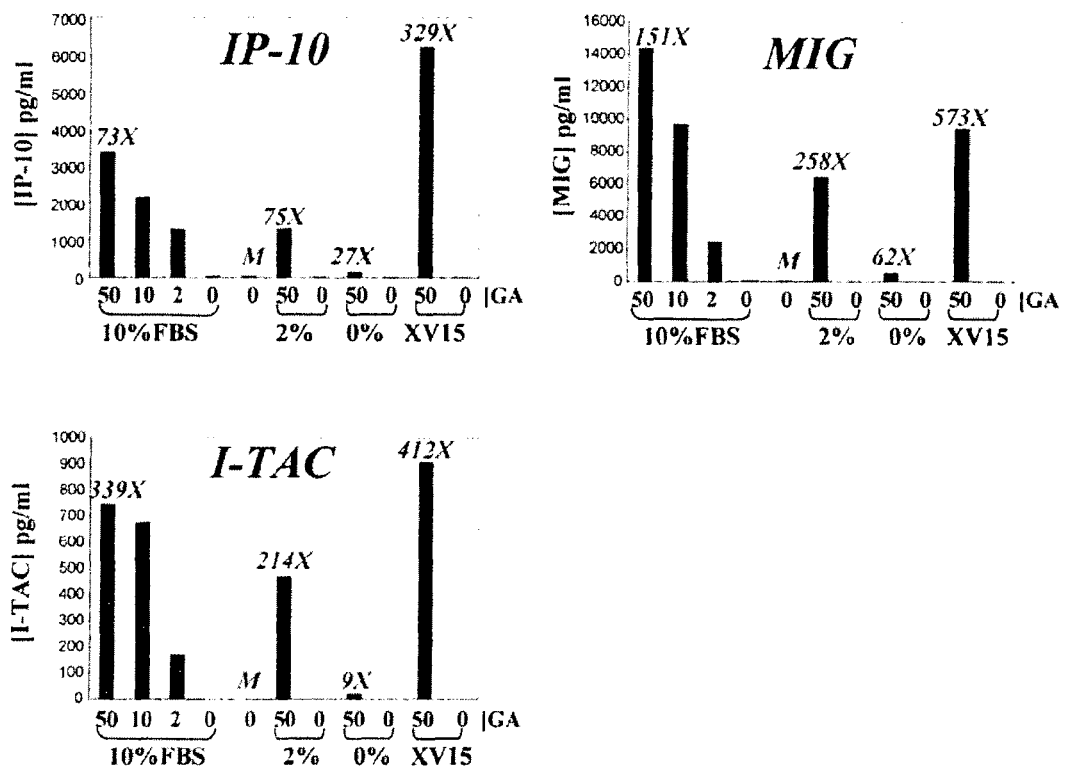

COPOLYMER ASSAY

This application is the National Stage of International Application No. PCT/US2008/067508, filed Jun. 19, 2008, which claims priority to and U.S. Provisional Patent Application Ser. No. 60/945,488, filed on Jun. 21, 2007. The contents of these applications are hereby incorporated by reference in their entireties.

FIELD

The presently disclosed subject matter generally relates to methods of characterizing complex peptide or polypeptide mixtures. More particularly, the presently disclosed subject matter relates to cell-based methods for evaluating one or more properties of an amino acid copolymer.

BACKGROUND

Copolymer-1 is a complex mixture of polypeptides prepared from the polymerization of the amino acids glutamic acid, lysine, alanine and tyrosine. Copolymer-1 also is known as glatiramer acetate and has the following structural formula:

(Glu,Ala,Lys,Tyr)$x$XCH$_3$COOH

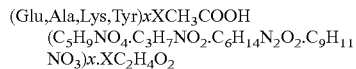

NO$_3$)$x$.XC$_2$H$_4$O$_2$

Glatiramer acetate (GA) is the active ingredient of COPAXONE® (Teva Pharmaceutical Industries Ltd., Israel), which comprises the acetate salts of synthetic polypeptides containing four naturally occurring amino acids: L-glutamic acid, L-alanine, L-tyrosine, and L-lysine, with a reported average molar fraction of 0.141, 0.427, 0.095, and 0.338, respectively.

Glatiramer acetate is used in the treatment of the relapsing-remitting form of multiple sclerosis (RRMS).

SUMMARY

The present invention provides methods and compositions for evaluating one or more properties of a candidate agent (e.g., an amino acid copolymer, e.g., Copolymer-1; e.g., glatiramer acetate). In one aspect, the invention provides a variety of embodiments for evaluating an amino acid copolymer preparation for physiological, pharmacodynamic, pharmacokinetic, or pharmaceutical properties including but not limited to potency, specificity, stability, biological activity, e.g., for suitability as a pharmaceutical preparation, e.g., for the treatment of autoimmune and/or inflammatory disease, disorders or dysfunctions.

In one embodiment, a method or assay described herein comprises (a) contacting (i) at least one cell that produces or secretes one or more proteins that are regulated by a pro-inflammatory molecule with (ii) an amount of an amino acid copolymer and (iii) the pro-inflammatory molecule, at a concentration and for a time sufficient to induce the cell(s) to produce or secrete the regulated protein. The production, secretion, induction, presence or level of the one or more regulated proteins (or a reporter gene for the one or more regulated proteins) can be detected and correlated with a property of the amino acid copolymer. In another embodiment, a method for evaluating an amino acid copolymer comprises: (a) providing at least one cell that is capable of a expressing protein that is induced by a cytokine; (b) contacting the at least one cell with an amount of the amino acid copolymer and the cytokine at a concentration and for a period of time sufficient to induce the cell to express the induced protein; (c) measuring the expression, secretion, induction, presense or level of the induced proteins; and (d) comparing the measured expression, secretion, induction, presense or level of the induced protein to a reference value, a cytokine induction profile or a pharmaceutical specification for a market pharmaceutical preparation of glatiramer acetate to evaluate a property of the amino acid copolymer. A cell that is capable of expressing a protein that is induced by a cytokine is a cell that will express more of the protein when exposed to the cytokine at a sufficient level than the cell will express in the absence of the cytokine. The cell may, of course, express the protein in the absence of the cytokine. The cell can be capable of expressing more than one protein that is induced by the cytokine. A cell that produces or secretes the protein is a cell that expresses the protein.

Also described is a method for evaluating a property of an amino acid copolymer comprising: (a) providing at least one cell that is capable of expressing a proteins that is induced by a cytokine; (b) contacting the at least one cell with an amount of the amino acid copolymer and the cytokine at a concentration and a period of time sufficient to induce the cell to express one or more proteins induced by the cytokine; and (c) detecting the induced protein to evaluate a property of the amino acid copolymer Also described is a method of evaluating a property of an amino acid copolymer, the method comprising: (a) providing at least one cell that is capable of secreting or producing one or more proteins regulated by a cytokine; (b) contacting the at least one cell with an amount of the amino acid copolymer and said cytokine at a concentration and a period of time sufficient to induce the cell to secrete or produce one or more proteins regulated by the cytokine; and (c) detecting the one or more regulated proteins to evaluate a property of the amino acid copolymer.

One or more properties of the amino acid copolymer preparation (e.g., of a test amino acid copolymer preparation), such as potency, specificity, stability, and/or biological activity, can be evaluated by comparing the results from the assay (e.g., a qualitative or quantitative test value corresponding to the induction, production, secretion, presence or level of a regulated protein) to a reference value, e.g., a value predetermined to correlate to a particular level of potency, specificity, stability, and/or biological activity of copolymer, e.g., a value predetermined to correlate with a level of potency, specificity, stability, and/or biological activity of the copolymer suitable for a pharmaceutical preparation useful to treat a disease, disorder, or dysfunction described herein. In one embodiment, the reference value is a cytokine induction profile, equivalence range or pharmaceutical specification for potency, specificity, stability, and/or biological activity for a marketed pharmaceutical preparation of glatiramer acetate. In other embodiments, the reference value is a value determined by direct measurement of a property of a reference compound, e.g., a reference glatiramer acetate preparation. In one embodiment, the test value is considered comparable to the reference value if it is within 25%, 20%, 15%, 10%, 5%, 2%, 1% or less of the reference value.

In one embodiment, the cell used in the assay is a leukocyte, e.g., a myeloid cell, e.g., a myeloid cell line or primary cell, e.g., blood mononuclear cell (e.g., T cells, natural killer cells, monocytes, macrophages, etc.), blood polymorphonuclear cell (e.g., eosinophils, basophils, neutrophils, megakaryocytes, etc.), dendritic cell, and thymic cells. The cell can be a tumorigenic myeloid cell line such as THP-1, U937, SiHa, or HL-60. Additionally, mammalian peripheral blood mononuclear cells as well as bone-marrow derived monocytes and monocytes may be used.

In one embodiment, the proinflammatory molecule is a pro-inflammatory cytokine, e.g., selected from the group consisting of tumor necrosis factor alpha (TNFα), interferon gamma (IFNγ), interleukin-1 beta (IL-1β), interleukin-6 (IL-6), and interleukin-8 (IL-8). In another embodiment, the proinflammatory molecule is LPS.

In one embodiment, the protein regulated by the proinflammatory molecule (whose induction, production, secretion, presence or level is detected in the assay) is a chemokine, e.g., an IFN-γ regulated chemokine. In one embodiment, the chemokine is selected from the group consisting of: γ-interferon-inducible protein 10 (IP-10), interferon-inducible T cell α-chemoattractant (I-TAC), monokine induced by γ-interferon (MIG). Other soluble proteins or cytokines induced by IFN-γ include those shown in Table 1. The induction, production, secretion, presence or level of a regulated protein can be detected directly, e.g., by an antibody-based method, such as an ELISA, or indirectly, e.g., by art-known techniques to detect transcripts for the protein or by use of a reporter gene assay.

In some embodiments, exposure of the cell(s) to the amino acid copolymer and the proinflammatory cytokine results in a synergistic induction of one or more of the cytokine-regulated proteins. In one example, exposure of myeloid cells to the amino acid copolymer (e.g., glatiramer acetate) and IFNγ results in a synergistic induction of one or more IFNγ-regulated chemokines or cytokines (e.g., of IP-10, I-TAC, MIG, and/or other CXCR3 ligands). In one embodiment, the induction of a regulated cytokine can be at least 5-fold, 10-fold, 20-fold, 30-fold, 40-fold, 50-fold, 75-fold, 100-fold, 150-fold, 200-fold, 300-fold or more over control values (e.g., over negative controls with no proinflammatory molecule and/or no copolymer).

The invention further provides a method of preparing a pharmaceutical composition of glatiramer acetate comprising preparing a batch of glatiramer acetate, evaluating the potency, specificity, biological activity and/or stability of the composition by a method described herein, and determining that the glatiramer acetate is acceptable for pharmaceutical use if at least a predetermined level of one or more proteins regulated by the cytokine is detected and/or if the regulated protein is induced to a level within 80%-125% (e.g., at least 80%, 85%, 90%, 95%, 98%, 100%, 110%, 115%, 120%, 125%) of a reference value.

Also described is a method for preparing a pharmaceutical composition comprising glatiramer acetate, comprising: polymerizing N-carboxy anhydrides of L-alanine, benzyl-protected L-glutamic acid, trifluoroacetic acid (TFA) protected L-lysine and L-tyrosine to generate a protected copolymer; treating the protected copolymer to partially depolymerize the protected copolymer and deprotect benzyl protected groups and deprotecting TFA-protected lysines to generate glatiramer acetate; and isolating the glatiramer acetate, wherein the improvement comprises: measuring the expression of a cytokine-induced protein in a myeloid cell or a primary myeloid cell line in the presence of a cytokine and a sample of the isolated glatiramar acetate and comparing the expression to reference value. In various embodiments of this preparation method: the cytokine is IFNγ; the improvement further comprises selecting the purified glatiramer acetate for use in the preparation of a pharmaceutical composition if the difference between the measured expression and the reference value is within a predetermined range; and the improvement further comprises: preparing a pharmaceutical composition comprising at least a portion of the selected purified glatiramer acetate.

Certain aspects of the presently disclosed subject matter having been stated hereinabove, which are addressed in whole or in part by the presently disclosed subject matter, other aspects will become evident as the description proceeds when taken in connection with the accompanying Examples and FIGURE as best described herein below.

BRIEF DESCRIPTION OF THE FIGURE

FIG. 1 illustrates the secretion of IP-10, I-TAC, and MIG over approximately 24 hours in various serum containing or serum-free media at a constant IFNγ concentration (10 ng/ml). The 10% FBS condition was tested at 50, 10, 2, and 0 μg/ml glatiramer acetate (GA). The 2% FBS, 0% FBS, and X-VIVO15 conditions were analyzed at 50 and 0 μg/ml GA. M represents the mannitol control carrier that was assayed at 100 μg/ml. The numbers above the bars represent the fold increase over the control (0 μg/ml).

DETAILED DESCRIPTION

The presently disclosed subject matter now will be described more fully hereinafter with reference to the accompanying FIGURE, in which some, but not all embodiments of the presently disclosed subject matter are shown. Many modifications and other embodiments of the presently disclosed subject matter set forth herein will come to mind to one skilled in the art to which the presently disclosed subject matter pertains having the benefit of the teachings presented in the foregoing descriptions and the associated FIGURE. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

Following long-standing patent law convention, the terms "a," "an," and "the" refer to "one or more" when used in this application, including the claims. Thus, for example, reference to "a sample" includes a plurality of samples, unless the context clearly is to the contrary (e.g., a plurality of samples), and so forth.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Overview

The present invention provides methods and compositions for evaluating one or more properties of a copolymer preparation which may be useful as a therapeutic preparation, e.g., for the treatment of an autoimmune, neurodegenerative, demyelinating or inflammatory disorder. The assays described herein may be in any format known in the art, including cell culture assays, organ culture assays, or ex vivo assays.

As used herein, a "copolymer", "amino acid copolymer" or "amino acid copolymer preparation" is a heterogeneous mixture of polypeptides consisting of a defined plurality of different amino acids (typically between 2-10, e.g., between 3-6, different amino acids). A copolymer may be prepared from the polymerization of individual amino acids, or may be produced recombinantly. The term "amino acid" is not limited to naturally occurring amino acids, but can include amino acid derivatives and/or amino acid analogs. For example, in an amino acid copolymer comprising tyrosine amino acids, one or more of the amino acids can be a homotyrosine. Further, an amino acid copolymer having one or more non-peptide or peptidomimetic bonds between two adjacent residues is included within this definition. A copolymer is non-uniform with respect to the molecular weight of each species of polypeptide within the mixture.

In one embodiment of the invention, the amino acid copolymer is a mixture of polypeptides comprising the amino acids Y, E, A, and K; Y, F, A, and K; V, Y, A, and K; V, W, A, and K; V, E, A, and K; Y, F, A, and K; V, W, A, and K; W, E, A and K, or F, E, A, and K. In another embodiment of the invention, the amino acid copolymer contains four different amino acids, each from a different one of the following groups: (a) lysine and arginine; (b) glutamic acid and aspartic acid; (c) alanine and glycine; (d) tyrosine and tryptophan. A specific copolymer according to this embodiment of the present invention comprises a mixture of polypeptides comprising alanine, glutamic acid, lysine, and tyrosine. In one embodiment, the copolymer comprises a mixture of polypeptides consisting of the amino acids Y, E, A, and K, also referred to as Copolymer 1 (Cop 1) or glatiramer acetate. In another embodiment, the amino acid copolymer contains three different amino acids each from a different one of three above mentioned groups (a) to (d), e.g., Y, A, and K; Y, E, and K; K, E, and A; or Y, E, and A.

In another embodiment, the amino acid copolymer comprises amino acids selected from the group consisting of alanine-glutamic acid-lysine-tyrosine-alanine (A-E-K-Y-A), alanine-glutamic acid-lysine-valine-alanine (A-E-K-V-A), alanine-glutamic acid-lysine-phenylalanine-alanine (A-E-K-F-A), alanine-lysine-tyrosine-alanine-glutamic acid (A-K-Y-A-E), glutamic acid-alanine-lysine-tyrosine-alanine (E-A-K-Y-A), alanine-lysine-valine-alanine-glutamic acid (A-K-V-A-E), and glutamic acid-alanine-lysine-valine-alanine (E-A-K-V-A), alanine-lysine-phenylalanine-alanine-glutamic acid (A-K-F-A-E), and glutamic acid-alanine-lysine-phenylalanine-alanine (E-A-K-F-A).

A "proinflammatory molecule" is a molecule that stimulates activation of leukocytes, epithelial cells, or stromal cells resulting in the amplification or propagation of an inflammatory immune response. A proinflammatory molecule can induce the production of activation markers (e.g., CD69, CD25, CD54, CD40 ligand, CD11b, CD62L, CD83, CD95) and/or secretion of other pro-inflammatory cytokines and/or chemokines from immune cells such as CD4 T cells, CD8 T cells, B cells, NK cells, monocytes, macrophages, dendritic cells, neutrophils, basophils, eosinophils, and mast cells. A proinflammatory cytokine is a small secreted protein that has the properties of a proinflammatory molecule as described herein, e.g., IFN-γ. This definition does not exclude molecules that may also have anti-inflammatory activity in some contexts.

A "chemokine" is a cytokine with chemotactic activity. Examples of chemokines include IL-8, RANTES, MIP-1a, MCP-1, IP-10, Mig, I-TAC, TARC, I-309.

The various methods described herein can be used to evaluate one or more properties of a test copolymer preparation, such as potency, specificity, stability, purity, and biological activity, by comparison of the test copolymer preparation to one or more predetermined reference value, such as a pharmaceutical specification value for potency, specificity, stability, and biological activity of glatiramer acetate. In some instances, a reference value can be determined by comparison to a known agent. This known agent is herein referred to as a "reference agent" or a "reference compound." A preferred reference agent of the invention is an amino acid copolymer (e.g., a pharmaceutical preparation of glatiramer acetate) that is suitable for use as a pharmaceutical preparation, e.g., it has been shown to have therapeutic efficacy in one or more autoimmune, degenerative, demyelinating and/or inflammatory disorders or conditions. By "therapeutic efficacy" is intended that the agent is capable of preventing, treating or ameliorating symptoms associated with the disorder or condition.

In one embodiment, the reference value is a predetermined pharmaceutical specification value for glatiramer acetate. In one embodiment, the reference compound is pharmaceutical preparation of glatiramer acetate. In one embodiment, the synergistic induction of cytokine-regulated proteins in various cell types when coadministered with exogenously supplied cytokine and copolymer-1 has been observed. As used herein, the term "synergistic" refers to two or more agents (e.g., glatiramer acetate and a cytokine) that are more effective in combination than the sum of the individual effects of each single agent alone. This synergistic induction of cytokine-regulated proteins can be used to screen a test copolymer preparation for properties, including biological activity, that are comparable to glatiramer acetate.

Glatiramer acetate is approved for reduction of the frequency of relapses in patients with relapsing-remitting multiple sclerosis. Multiple sclerosis has been classified as an autoimmune disease. Glatiramer acetate has also been disclosed for use in the treatment of other autoimmune diseases, inflammatory non-autoimmune diseases and to promote nerve regeneration and/or to prevent or inhibit secondary degeneration which may follow primary nervous system injury Furthermore, glatiramer acetate has been disclosed as a treatment for immune mediated diseases as well as diseases associated with demyelination. The methods described herein can be used to evaluate the activity of a glatiramer acetate preparation for suitability as a pharmaceutical preparation for any of these disorders.

In Vitro Assays

The methods and compositions of the present invention comprise assays useful for evaluating one or more properties of a candidate agent (e.g., an amino acid copolymer). In one embodiment, a test copolymer preparation is screened using an in vitro assay to evaluate the effect of the copolymer preparation on the production and/or secretion of one or more proteins regulated by a proinflammatory cytokine. The level of proinflammatory cytokine-regulated induction of the protein(s) in the presence of a test copolymer preparation is compared to the level of the proinflammatory cytokine-regulated induction of that protein(s) in the same cell type in the presence of a reference agent. The level (i.e., qualitative or quantitative level) and nature (i.e., species of protein) of induction is referred to herein as the "cytokine induction profile." The cytokine induction profile can be used to assess one or more properties of an amino acid copolymer, such as potency, stability, specificity, and biological activity. In one embodiment, a test copolymer preparation is said to be suitable as a pharmaceutical composition when the cytokine induction profile of the test copolymer preparation (e.g., the level of induction or the number of similar proteins that are induced, or both) is between about 80% and about 125%, including about 85%, about 90%, about 91%, about 92%, about 93%, about 94%, about 95%, about 96%, about 97%, about 98%, about 99%, about 100%, about 105%, about 110%, about 115%, about 120%, up to about 125% of a reference value or profile for a copolymer pharmaceutical composition (e.g., a lot of COPAXONE®). In another embodiment, a test copolymer preparation is said to have substantially the same properties as a reference copolymer preparation (e.g., COPAXONE®) when the cytokine induction profile of the test copolymer preparation (e.g., the level of induction or the number of similar proteins that are induced, or both) is between about 80% and about 125%, including about 85%, about 90%, about 91%, about 92%, about 93%, about 94%, about 95%, about 96%, about 97%, about 98%, about 99%, about 100%, about 105%, about 110%, about 115%, 120%, up to about 125% of the reference copolymer preparation.

In one embodiment, the reference is an amino acid copolymer with known therapeutic efficacy in one or more autoimmune or inflammatory disorders. In a specific embodiment, the reference agent is glatiramer acetate. The reference value can be a value predetermined to correspond to a certain level of potency, purity, stability or other activity of glatiramer acetate.

One or more cells capable of producing or secreting a cytokine-regulated protein is contacted with a candidate agent or a reference agent at a concentration and time sufficient for the induction of the cytokine-regulated protein. The assay may comprise two or more cell types, which may be primary cells, cell lines, or combinations thereof. The concentration and time sufficient for the induction of the cytokine-regulated protein is that which results in the detectable production or secretion of the cytokine-regulated protein above the level of that protein in the absence of the candidate or reference agent (e.g., above baseline levels of the protein that is regulated by the cytokine). The concentration of the candidate agent may be present in the assay medium at a concentration of at least about 0.05 µg/mL, at least about 1 µg/mL, at least about 2 µg/mL, at least about 3, about 4, about 5, about 6, about 7, about 8, about 9, about 10, about 15, about 20, about 25, about 30, about 40, about 50, about 60, about 70, about 80, about 90, about 100, about 110, about 125, about 150, about 175, about 200, about 225, about 250, about 275, about 300, about 375, about 400, about 425, about 450, about 475, at least about 500 µg/mL or greater, so long as the concentration does not reach that which is cytotoxic.

The candidate agent or reference agent may be incubated (i.e., "contacted") with the cell capable of secreting or producing the cytokine-regulated protein for at least about 1 hour, at least about 1.5 hours, at least about 2 hours, at least about 3 hours, at least about 4 hours, about 5 hours, about 6 hours, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 40, about 45, about 48 or more hours.

In one embodiment, an amount of the proinflammatory cytokine that regulates the expression of the protein described above may be added exogenously to the assay medium. The cytokine can be added before, at the same time as, or after the addition of the test or reference copolymer preparation. In one embodiment, the cytokine is added at the same time as the test or reference copolymer preparation. The cytokine can be present in the assay medium at a concentration of at least about 1 ng/ml, at least about 2 ng/ml, at least about 3, about 4, about 5, about 6, about 7, about 8, about 9, about 10, about 15, about 20, about 25, about 30, about 40, at least about 50 ng/ml or greater, so long as the concentration does not reach that which is cytotoxic. In some embodiments, the cytokine can be heterologously expressed in the host cell of the assay. The heterologous gene can be under the control of a constitutive or an inducible promoter.

In various aspects of the present invention, the cytokine that regulates the production and secretion of the one or more proteins described herein is a proinflammatory cytokine. Proinflammatory cytokines are typically associated with a Th1 T cell response. In one embodiment, the proinflammatory cytokine is selected from the group that includes, but is not limited to, TNFα, interferon gamma (IFNγ), interleukin-1 (IL-1), interleukin-1 beta (IL-1β), interleukin-1 (IL-2) interleukin-6 (IL-6), interleukin-4 (IL-4), interleukin-8 (IL-8), interleukin-10 (IL-10), interleukin-13 (IL-13), interleukin-17 (IL-17), interleukin-18 (IL-18), interleukin-23 (IL-23), and lymphotoxin-α. In the assays described herein, the cytokine is present at a concentration sufficient to induce the production or secretion of one or more proteins regulated by that cytokine In one embodiment, the cytokine-regulated protein comprises proteins (e.g., chemokines) that are regulated by interferon gamma, including γ-interferon-inducible protein 10 (IP-10), interferon-inducible T cell α-chemoattractant (1-TAC), and monokine induced by γ-interferon (MIG). IP-10, MIG, and I-TAC are expressed within CNS lesions in both Experimental Autoimmune Encephalitis (EAE) and multiple sclerosis (MS), and the receptor that binds these ligands, CXCR3, is expressed on T cells infiltrating EAE and MS lesions as well as on T cells in the cerebrospinal fluid and periphery of MS patients during exacerbations (reviewed in Klein et al. (2004) *J Immunol* 172:550-559).

Cells

Many cell types find use in the methods of the present invention so long as they are capable of producing one or more proteins regulated by the cytokines described herein. Included, without limitation, are cells involved in inflammatory responses, e.g., myeloid cell lines or primary cells, e.g., blood mononuclear cells (e.g., T cells, natural killer cells, monocytes, macrophages, etc.), blood polymorphonuclear cells (e.g., eosinophils, basophils, neutrophils, megakaryocytes, etc.), and dendritic cells; and thymic epithelial cells. Tumorigenic cell lines such as THP-1, U937, SiHa, and HL-60 are also included. Other useful cells may include epithelial cells, stromal cells, and endothelial cells, e.g., primary microvasculature, HUVEC, aortic endothelial cells. Additionally, mammalian peripheral blood mononuclear cells as well as bone-marrow derived monocytes and monocytes isolated by elutriation or negative magnetic bead isolation may also be used.

Cell Culture Conditions

Cell culture media formulations are well known in the literature and many are commercially available. In one embodiment, the cells in the assay are cultured in serum-free media. Methods for preparing serum-free media are well known in the art. The ingredients may include amino-acids (both D and/or L-amino acids) such as glutamine, alanine, arginine, asparagine, cystine, glutamic acid, glycine, histidine, isoleucine, leucine, lysine, methionine, phenylalanine, proline, serine, threonine, tryptophan, tyrosine, and valine and their derivatives; acid soluble subgroups such as thiamine, ascorbic acid, ferric compounds, ferrous compounds, purines, glutathione and monobasic sodium phosphates.

Additional ingredients may include sugars, deoxyribose, ribose, nucleosides, water soluble vitamins, riboflavin, salts, trace metals, lipids, acetate salts, phosphate salts, HEPES, phenol red, pyruvate salts and buffers.

Other ingredients often used in media formulations include fat soluble vitamins (including vitamins A, D, E and K), steroids and their derivatives, cholesterol, fatty acids and lipids, Tween 80, 2-mercaptoethanol pyramidines, as well as a variety of supplements including serum (fetal, horse, calf, etc.), proteins (insulin, transferrin, growth factors, hormones, etc.), antibiotics (gentamicin, penicillin, streptomycin, amphotericin B, etc.), whole egg ultra filtrate, and attachment factors (fibronectins, vitronectins, collagens, laminins, tenascins, etc.). It is well within the skilled artisan to determine the appropriate conditions under which to propagate a cell useful in the methods of the present invention.

The cells may be cultured in any manner known in the art including in suspension, in monolayer, on beads or in three-dimensions. Methods of cell and tissue culturing are well known in the art, and are described, for example, in Cell & Tissue Culture: Laboratory Procedures; Freshney (1987), Culture of Animal Cells: A Manual of Basic Techniques.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (2001) *Molecular Cloning A Laboratory Manual* (3d Lab Edition; Cold Spring Harbor Laboratory Press); Wu et al., eds., *Methods In Enzymology*, Vols. 154 and 155; Mayer and Walker, eds. (1988) *Immunochemical Methods In Cell And Molecular Biology* (Academic Press, London); Herzenberg, Weir and Blackwell, eds., (1996) *Weir's Handbook Of Experimental Immunology*, Volumes I-IV.

Measurement of Protein Induction

Induction of a cytokine-regulated protein as described herein can be evaluated in a variety of different ways, each of which is known to those of skill in the art. The measurement may be either quantitative or qualitative, so long as the measurement is capable of indicating whether the level of the cytokine-regulated protein of interest in the sample is at, above, or below a reference value. The level of induction, as well as the specific proteins that are induced, of one or more of the cytokine-regulated proteins (herein referred to as the "cytokine induction profile") can be compared to a reference cytokine induction profile (e.g., a profile that has been predetermined to correspond to a particular activity or level of activity) or to the cytokine induction profile of one or more of a reference agent and a negative control agent. A negative control agent can be, e.g., one that has no potency or activity, or one that does not induce cytokine-regulated protein production in the cell type utilized in the assay, or both.

The cytokine induction profile can be used as a measure of a biological property or activity. Properties such as potency, specificity, and stability can be evaluated using the cytokine induction profile. For the purposes of the present invention, potency and biological activity are evaluated by evaluating the level of induction of one or more cytokine-regulated proteins. "Specificity" is evaluated, e.g., by identifying or distinguishing the tested preparation as being glatiramer acetate vs not glatiramer acetate based on the results. Stability can be evaluated by comparing the cytokine induction profile of the candidate agent to the reference agent over time. In some embodiments, the cytokine induction profile can be used as a measure of equivalence to a reference agent.

In one embodiment, induction of the cytokine-regulated protein is detected using an immunological method. Immunological methods which can be used to detect cytokine-regulated protein induction include, but are not limited to, competitive and non-competitive assay systems using immune-based techniques such as Western blots, radioimmunoassays, ELISA (enzyme linked immunosorbent assay), multiplex ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. Such assays are routine and known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise obtaining supernatant from the assay media (optionally supplemented with protein phosphatase and/or protease inhibitors, e.g., ethylenediaminetetraacetic acid (EDTA), phenylmethanesulphonylfluoride (PMSF), aprotinin, sodium vanadate), adding a binding molecule of interest (i.e., a molecule, such as an antibody, that specifically binds to the cytokine-regulated protein of interest) to the supernatant, incubating for a period of time (e.g., 1 to 4 hours) at about 4° C., adding protein A and/or protein G sepharose beads to the cell lysate, incubating for about an hour or more at about 4° C., washing the beads in buffer and resuspending the beads in sodium dodecyl sulfate (SDS)/sample buffer. The ability of the binding molecule of interest to immunoprecipitate a particular antigen can be assessed by, e.g., Western blot analysis. One of skill in the art would be knowledgeable as to the parameters that can be modified to increase the binding of the binding molecule to a cytokine-regulated protein and decrease the background (e.g., pre-clearing the supernatant with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1, which is hereby incorporated by reference herein in its entirety.

Western blot analysis generally comprises preparing protein samples from the assay supernatant, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with the binding molecule of interest (e.g., an antibody specific for the cytokine-regulated protein of interest) diluted in blocking buffer, washing the membrane in washing buffer, blocking the membrane with an antibody (which recognizes the binding molecule, e.g., a secondary antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the cytokine-regulated protein. One of skill in the art would be knowledgeable as to the parameters that can be modified to increase the signal detected and to reduce the background noise. For further discussion regarding Western blot protocols see, e.g., Ausubel et al., eds, 1994, Current Protocols in Molecular Biology, Vol. 1, John Wiley & Sons, Inc., New York at 10.8.1, which is hereby incorporated by reference herein in its entirety.

ELISAs comprise preparing cytokine-regulated protein, coating the well of a 96-well microtiter plate with the cytokine-regulated protein of interest or an assay supernatant comprising the cytokine-regulated protein of interest, adding the binding molecule of interest conjugated to a detectable compound such as an enzymatic substrate (e.g., horseradish peroxidase or alkaline phosphatase) to the well and incubating for a period of time, and detecting the presence of the cytokine-regulated protein. In ELISAs, the binding molecule of interest does not have to be conjugated to a detectable compound; instead, an antibody (which recognizes the binding molecule of interest) conjugated to a detectable compound may be added to the well. Further, instead of coating the well with the cytokine-regulated protein of interest or an assay supernatant comprising the cytokine-regulated protein of interest, the binding molecule may be coated to the well. In this case, an antibody conjugated to a detectable compound may be added following the addition of the cytokine-regulated protein of interest or an assay supernatant comprising the cytokine-regulated protein of interest to the coated well. One of skill in the art would be knowledgeable as to the parameters that can be modified to increase the signal detected as well as other variations of ELISAs known in the art. For further discussion regarding ELISAs see, e.g., Ausubel et al, eds., 1994, Current Protocols in Molecular Biology, Vol. 1, John Wiley & Sons, Inc., New York at 11.2.1, which is hereby incorporated by reference herein in its entirety. Various ELISA kits may be obtained from commercial sources such as BioSource International (Montreal, Canada), BD Biosciences (San Jose, Calif.), R&D Systems (Minneapolis, Minn.), Millipore Corp. (Bedford, Mass.), and Pierce (Rockville, Ill.).

Affinity-based measurements that utilize a molecule that specifically binds to the cytokine-regulated protein being measured (an "affinity reagent," such as an antibody or aptamer) may also be used, as well as other technologies, such as spectroscopy-based technologies (e.g., matrix-assisted laser desorption ionization-time of flight, or MALDI-TOF, spectroscopy).

Affinity-based technologies include antibody-based assays (immunoassays as described above) and assays utilizing aptamers (nucleic acid molecules which specifically bind to other molecules), such as ELONA. Additionally, assays utilizing both antibodies and aptamers are also contemplated (e.g., a sandwich format assay utilizing an antibody for capture and an aptamer for detection). Generally, aptamers may be substituted for antibodies in nearly all formats of immunoassay, although aptamers allow additional assay formats (such as amplification of bound aptamers using nucleic acid amplification technology such as PCR (U.S. Pat. No. 4,683, 202) or isothermal amplification with composite primers (U.S. Pat. Nos. 6,251,639 and 6,692,918).

Affinity-based assays may be in competition or direct reaction formats, utilize sandwich-type formats, and may further be heterogeneous (e.g., utilize solid supports) or homogenous (e.g., take place in a single phase) and/or utilize immunoprecipitation. Most assays involve the use of labeled affinity reagent (e.g., antibody, polypeptide, or aptamer); the labels may be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA and ELONA assays.

In a heterogeneous format, the assay utilizes two phases (typically aqueous liquid and solid). Typically a cytokine-regulated protein-specific affinity reagent is bound to a solid support to facilitate separation of the cytokine-regulated protein from the bulk of the sample. After reaction for a time sufficient to allow for formation of affinity reagent/cytokine-regulated protein complexes, the solid support or surface containing the antibody is typically washed prior to detection of bound polypeptides. The affinity reagent in the assay for measurement of cytokine-regulated proteins may be provided on a support (e.g., solid or semi-solid); alternatively, the polypeptides in the sample can be immobilized on a support or surface. Examples of supports that can be used are nitrocellulose (e.g., in membrane or microtiter well form), polyvinyl chloride (e.g., in sheets or microtiter wells), polystyrene latex (e.g., in beads or microtiter plates), polyvinylidine fluoride, diazotized paper, nylon membranes, activated beads, glass and Protein A beads. Both standard and competitive formats for these assays are known in the art.

Array-type heterogeneous assays are suitable for measuring levels of cytokine-regulated proteins when the methods of the invention are practiced utilizing multiple cytokine-regulated proteins. Array-type assays used in the practice of the methods of the invention will commonly utilize a solid substrate with two or more capture reagents specific for different cytokine-regulated proteins bound to the substrate in a predetermined pattern (e.g., a grid). The sample (e.g., assay supernatant) is applied to the substrate and cytokine-regulated proteins in the sample are bound by the capture reagents. After removal of the sample (and appropriate washing), the bound cytokine-regulated proteins are detected using a mixture of appropriate detection reagents that specifically bind the various cytokine-regulated proteins. Binding of the detection reagent is commonly accomplished using a visual system, such as a fluorescent dye-based system. Because the capture reagents are arranged on the substrate in a predetermined pattern, array-type assays provide the advantage of detection of multiple cytokine-regulated proteins without the need for a multiplexed detection system.

In a homogeneous format the assay takes place in single phase (e.g., aqueous liquid phase). Typically, the sample is incubated with an affinity reagent specific for the cytokine-regulated protein in solution. For example, it may be under conditions that will precipitate any affinity reagent/antibody complexes which are formed. Both standard and competitive formats for these assays are known in the art.

In a standard (direct reaction) format, the level of cytokine-regulated protein/affinity reagent complex is directly monitored. This may be accomplished by, for example, determining the amount of a labeled detection reagent that forms in bound to cytokine-regulated protein/affinity reagent complexes. In a competitive format, the amount of cytokine-regulated protein in the sample is deduced by monitoring the competitive effect on the binding of a known amount of labeled cytokine-regulated protein (or other competing ligand) in the complex. Amounts of binding or complex formation can be determined either qualitatively or quantitatively.

In addition to immunoassays, induction can be measured by evaluating patterns of expression of the genes encoding the cytokine-regulated proteins, or of reporter genes. For example, expression patterns can be evaluated by Northern analysis, PCR, RT-PCR, Taq Man analysis, ribonuclease protection assays, FRET detection, monitoring one or more molecular beacons, hybridization to an oligonucleotide array, hybridization to a cDNA array, hybridization to a polynucleotide array, hybridization to a liquid microarray, hybridization to a microelectric array, cDNA sequencing, clone hybridization, cDNA fragment fingerprinting, and the like. The particular method elected will be dependent on such factors as quantity of RNA recovered, artisan preference, available reagents and equipment, detectors, and the like.

As will be understood by those of skill in the art, the mode of detection of the signal will depend on the exact detection system utilized in the assay. For example, if a radiolabeled detection reagent is utilized, the signal will be measured using a technology capable of quantitating the signal from the sample or of comparing the signal from the sample with the signal from a reference sample, such as scintillation counting, autoradiography (typically combined with scanning densitometry), and the like. If a chemiluminescent detection system is used, then the signal will typically be detected using a luminometer. Methods for detecting signal from detection systems are well known in the art and need not be further described here.

When more than one cytokine-regulated protein is measured, the sample may be divided into a number of aliquots, with separate aliquots used to measure different cytokine-regulated protein (although division of the sample into multiple aliquots to allow multiple determinations of the levels of the cytokine-regulated protein in a particular sample are also contemplated). Alternately the sample (or an aliquot therefrom) may be tested to determine the levels of multiple cytokine-regulated protein in a single reaction using an assay capable of measuring the individual levels of different cytokine-regulated protein in a single assay, such as an array-type assay or assay utilizing multiplexed detection technology (e.g., an assay utilizing detection reagents labeled with different fluorescent dye markers).

It is common in the art to perform "replicate" measurements. Replicate measurements are ordinarily obtained by splitting a sample into multiple aliquots, and separately measuring the biomarker(s) in separate reactions of the same assay system. Replicate measurements are not necessary to the methods of the invention, but many embodiments of the invention will utilize replicate testing, particularly duplicate and triplicate testing. In some embodiments, the reference agent and the candidate agent will be assayed using separate aliquots of cells obtained from the same cell culture. In another embodiment, the reference agent (and/or negative control) and the candidate agent will be assayed using the same batch of cells. In this embodiment, each agent is assayed at different times, the assay media is replaced between measurements, and the cells are allowed to recover to an appropriate cell density following each measurement.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

The process of comparing a measured value and a reference value can be carried out in any convenient manner appropriate to the type of measured value and reference value for the cytokine-regulated protein at issue. As discussed above, "measuring" can be performed using quantitative or qualitative measurement techniques, and the mode of comparing a measured value and a reference value can vary depending on the measurement technology employed. For example, when a qualitative colorimetric assay is used to measure cytokine-regulated protein levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values (e.g., quantitative measurements of concentration, such as nanograms of cytokine-regulated protein per milliliter of sample, or absolute amount). In other examples, measured values are qualitative. As with qualitative measurements, the comparison can be made by inspecting the numerical data, or by inspecting representations of the data (e.g., inspecting graphical representations such as bar or line graphs).

A measured value is generally considered to be substantially similar to a reference value if it is about 80% to about 125% of the reference value.

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a cytokine-regulated protein. Alternately, a separate device (e.g., a digital computer) may be used to compare the measured value(s) and the reference value(s). Automated devices for comparison may include stored reference values for the cytokine-regulated protein(s) being measured, or they may compare the measured value(s) with reference values that are derived from contemporaneously measured reference samples (e.g., glatiramer acetate samples).

As will be apparent to those of skill in the art, when replicate measurements are taken for the biomarker(s) tested, the measured value that is compared with the reference value is a value that takes into account the replicate measurements. The replicate measurements may be taken into account by using either the mean or median of the measured values as the "measured value."

Method of Preparing Glatiramer Acetate

The methods and compositions of the present invention are useful for evaluating one or more properties of a batch of glatiramer acetate. The methods comprise preparing a batch of glatiramer acetate, evaluating one or more of stability, specificity, potency, and biological activity using the assays described herein, and comparing the properties of the batch of glatiramer acetate to those of a reference compound (e.g., a standardized batch of glatiramer acetate, e.g., one that has been approved for therapeutic use) or reference value for a reference compound (e.g., a pharmaceutical specification for glatiramer acetate). The batch of glatiramer acetate is said to be acceptable for pharmaceutical use if at least a predetermined level of one or more cytokine-regulated proteins is detected. The "predetermined level" is that which can be detected using the reference compound or that which is specified in a pharmaceutical specification for glatiramer acetate.

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. Thus, the following Examples are offered by way of illustration and not by way of limitation.

EXAMPLES

Example 1

Copolymer Assay

Methods

THP-1 cells (ATCC, TIB-202) were received from the American Type Culture Collection (ATCC). The THP-1 cells were shown to be free of mycoplasma contamination using a multi-media direct culture assay combined with an indicator cell-DNA fluorochrome staining assay (cat. # M-250, Bionique Testing Laboratories, Inc., Saranac Lake, N.Y.). Cells were grown in complete growth medium and incubated in a 37° C., 5% $CO_2$ incubator.

Assay medium was prepared fresh the day of the assay. The assay medium consisted of 2 mM Glutamax I Supplement (Invitrogen, 35050-79) in X-VIVO 15 serum-free medium (Cambrex, 04-418Q). These reagents were filtered in a 0.2 micron cellulose acetate filter unit (Nalgene, 156-4020). After filtration, the bottle was covered with foil to protect the medium from light.

COPAXONE® (glatiramer acetate; Teva Pharmaceuticals) was stored in the manufacturer's syringe at 4° C. Samples were prepared at a 2× concentration in the 2×IFN-γ assay medium in sterile, siliconized microfuge tubes. Final concentrations from 0 μg/ml to 400 μg/ml were tested in the assay.

Human IFN-γ (R&D Systems, 285-IF-100) was reconstituted with sterile 0.2% bovine serum albumin (BSA) in phosphate-buffered saline (PBS) (Chemicon, 3225-80).

On the day prior to assay, THP-1 cells were seeded at $2\times10^5$ cells/ml (20 ml final volume). These cells were harvested by centrifugation at 400×g, 5 min, 18° C. Cells were washed once with assay medium (without IFN-γ) and resuspended in assay medium (without IFN-γ) and counted. THP-1 cells were resuspended at $5\times10^5$ cells/ml in assay medium (with 0, 1, 10, and 100 ng/ml final concentration of IFN-γ). Cells were seeded from low to high concentrations of glatiramer acetate (50, 10, 2, and 0 ng/ml) at 50 μl per well with a multi-channel pipettor. Assay plates were incubated for 0 to 23 hours in a 37° C., 5% $CO_2$ incubator.

Conditioned medium was harvested into non-sterile, siliconized tubes. Tubes were centrifuged at 400×g, 5 min, 4° C. The supernatants were transferred to new, siliconized tubes and flash frozen in liquid nitrogen. Frozen conditioned medium was stored at −80° C. until they were submitted for Searchlight multiplex cytokine analysis (Pierce Endogen, Woburn, Mass.).

Results

Effect of COPAXONE® on a Wide Panel of Proteins:

The effect of COPAXONE®, in combination with IFN-γ, on secretion of a broad panel of cytokines, chemokines, soluble receptors, and proteases from THP-1 cells was examined. Addition of COPAXONE®, induced a striking increase in the secretion of the chemokine, IP-10 (Table 1). IP-10 is an IFN-γ-regulated chemokine which binds to the CXCR3 receptor. Interestingly, COPAXONE® treatment also resulted in higher levels of IFN-γ observed in the culture medium at 24 hr, even though IFN-γ was added exogenously at the start of the experiment. The effect of COPAXONE® on IFN-γ production may account in part for its synergistic action on IP-10 secretion. Other chemokines such as MCP-1 and MDC, which bind to the CCR2 and CCR4 receptors, respectively, also showed a robust secretory response to COPAXONE®, although the magnitude of the induction was not as high as that observed with IP-10 (Table 1). Similarly, other cytokines, such as IL6, showed a synergistic response to COPAXONE® and IFN-γ. Some chemokines, such as RANTES and TARC, and cytokines, such as IL-10, IL12, p70, TNFalpha, TIMP1, and MMP9 showed small increases with COPAXONE® treatment.

TABLE 1

Effect of COPAXONE ® treatment on chemokine and cytokine secretion from THP-1 cells

| Chemokines | IP10 | MCP1 | MDC | I309 | IL-8 | MIP1α | RANTES | TARC |
|---|---|---|---|---|---|---|---|---|
| IFNγ alone (10 ng/ml) | 17.9* | 32.3* | 2.2* | 1.6* | 25.6* | 10.5* | 96.7* | 11.7* |
| IFNγ + 50 μg/ml I356 | 4060.5* | 688.2* | 23.6* | 15.6* | 217.1* | 73.9* | 352.2* | 35.2* |
| Fold-increase | 226.3 | 21.3 | 10.6 | 9.7 | 8.5 | 7.1 | 3.6 | 3.0 |

| Cytokines | IFNγ | IL-6 | IL1β | IL-10 | IL12p70 | TNFα |
|---|---|---|---|---|---|---|
| IFNγ alone (10 ng/ml) | 470.9* | 0.2* | 0.2* | 0.4* | 4.6* | 33.3* |
| IFNγ + 50 μg/ml I356 | 4575.9* | 3.8* | 0.5* | 0.7* | 8.9* | 61.3* |
| Fold-increase | 9.7 | 19.0 | 2.4 | 2.0 | 1.9 | 1.8 |

| Receptors/Proteases | ICAM1 | MMP2 | TNFR1 | TNFR2 | TIMP1 | MMP9 |
|---|---|---|---|---|---|---|
| IFNγ alone (10 ng/ml) | 46.4* | 158.2* | 6.9* | 11.0* | 3848.4* | 39.1* |
| IFNγ + 50 μg/ml I356 | 279.9* | 915.9* | 35.8* | 34.4* | 6364.3* | 8.9* |
| Fold-increase | 6.0 | 5.8 | 5.2 | 3.1 | 1.7 | 0.2 |

*pg/ml

Synergistic Effects:

Some embodiments of the assay show a synergistic effect. FIG. 1 illustrates the synergistic effect of COPAXONE® and IFN-γ on the secretion of IP-10 and other chemokines THP-1 cells treated with IFN-γ alone showed only a modest production of IP-10, I-TAC, and MIG (all CXCR3 ligands). The addition of COPAXONE® in combination with IFN-γ, induced a striking, concentration-dependent effect on secretion of all three chemokines The levels of IP-10, I-TAC, and MIG secreted in the presence of 50 μg/ml COPAXONE® and 10 ng/ml IFN-γ were 329-, 412-, and 573-fold higher, respectively, than baseline containing IFN-γ alone. IFN-γ levels measured at 24 hours also showed a concentration-dependent increase with COPAXONE® treatment. The THP-1 cells were cultured in the presence of various concentrations of fetal bovine serum (FBS) or in X-VIVO15 serum-free medium. COPAXONE® induced a robust secretion of all three chemokines, IP-10, MIG and I-TAC, as well as secretion of IFN-γ in all conditions; however, cells cultured in the X-VIVO15 serum-free defined medium showed the highest fold induction over baseline. A similar response was seen with two other human myeloid cell lines, U-937 and HL-60; and with primary human dendritic cells.

Table 2 shows the fold-induction for IP-10, I-TAC, and MIG with COPAXONE® and IFN-γ treatment over IFN-γ alone at 23 hours. The fold-induction over baseline is maximal at 1-10 ng/ml IFN-γ. Importantly, THP-1 cells do not produce any significant amount of IP-10 when treated with COPAXONE® in the absence of IFN-γ, and IFN-γ alone (in the absence of COPAXONE®) induces only small amounts of chemokine secretion. The synergistic effect of COPAXONE® and IFN-γ is clearly illustrated in Table 2. Lower levels of IP-10, I-TAC and MIG can be detected in the assay as early as 3-6 hours of treatment with COPAXONE® and the higher IFN-γ concentrations; however, the dynamic range is better at 18-24 hours at which lower IFN-γ concentrations can be used.

TABLE 2

Chemokine induction at 23 hours (expressed as fold increase over the control (0))

| | IP-10 GA (µg/ml) | | | I-TAC GA (µg/ml) | | | MIG GA (µg/ml) | | |
|---|---|---|---|---|---|---|---|---|---|
| | 0 | 2 | 10 | 0 | 2 | 10 | 0 | 2 | 10 |
| IFNγ 0 ng/ml | 0 | 0 | 0 | 1 | 1 | 4 | 1 | 1 | 1 |
| IFNγ 10 ng/ml | 1 | 72 | 233 | 1 | 10 | 51 | 1 | 21 | 284 |
| IFNγ 100 ng/ml | 1 | 49 | 67 | 1 | 46 | 113 | 1 | 39 | 333 |
| IFNγ 1000 ng/ml | 1 | 13 | 14 | 1 | 23 | 49 | 1 | 23 | 160 |

Dose Dependence:

Table 3 shows the concentration dependence of the assay. pg/ml values with standard deviations are shown for IFN-γ (10 ng/ml) mediated induction of IP-10, I-TAC, and MIG at each concentration of glatiramer acetate (GA). Each value represents 12 samples from 6 independent THP-1 assays with duplicate points, each measured at 22-24 hours of incubation. In this case, the readout was Endogen Searchlight multiplex ELISA assay. The absolute pg/ml numbers will be different depending on the detection method. For example, one may see a 5-10 fold difference between the Endogen Searchlight multiplex ELISA assay and a standard ELISA. Absolute numbers will also be different depending on the time of incubation and concentration of IFN-γ. Nonetheless, within the same assay format and method, the assay can be used to compare two or more copolymer preparations and/or to determine a reference value (e.g., an equivalence range) for comparison to values obtained with a test preparation.

TABLE 3

Glatiramer acetate (GA) dose dependence

| [GA] mg/ml | IP-10 pg/ml ± Std. Dev. | | I-TAC pg/ml ± Std. Dev. | | MIG pg/ml ± Std. Dev. | |
|---|---|---|---|---|---|---|
| 0 | 13.5 | 2.8 | 3.2 | 0.8 | 13.6 | 2.3 |
| 0.78 | 259.2 | 69.1 | 16.5 | 5.2 | 149.7 | 33.2 |
| 1.56 | 483.7 | 87 | 42.1 | 12.8 | 345.6 | 69.3 |
| 3.13 | 580.8 | 107 | 82.6 | 9.1 | 933.6 | 132.9 |
| 6.25 | 581.4 | 124.7 | 105.9 | 15 | 2704.5 | 650.9 |
| 12.5 | 782.6 | 179.9 | 179.2 | 21.9 | 3608 | 635.2 |
| 25 | 829 | 135.2 | 247.1 | 41 | 4480.6 | 726.4 |
| 50 | 2150.8 | 840.1 | 532.6 | 129.4 | 13771.2 | 5694 |

TABLE 3-continued

Glatiramer acetate (GA) dose dependence

| [GA] mg/ml | IP-10 pg/ml ± Std. Dev. | | I-TAC pg/ml ± Std. Dev. | | MIG pg/ml ± Std. Dev. | |
|---|---|---|---|---|---|---|
| 100 | 12865.1 | 1839.5 | 2444 | 238.4 | 45353.3 | 8983.7 |
| 200 | 10899 | 1933.7 | 2091.2 | 250.9 | 37897.5 | 8052.1 |
| 400 | 6111.3 | 976.7 | 1560.5 | 220.8 | 27574.5 | 4725.5 |

Summary

This example shows that the glatiramer acetate-mediated induction of cytokines, e.g., chemokines IP-10, MIG and I-TAC, in response to stimulation from a pro-inflammatory cytokine (e.g., IFN-γ) can be used to evaluate the activity (e.g., one or more of: potency, purity, stability across time, biological activity or equivalence to a reference standard) of glatiramer acetate. Generally, a sample having a greater enhancement within a comparative assay correlates with greater potency or stability.

The glatiramer acetate-mediated enhancement of secretion of IP-10, MIG, and I-TAC in the presence of IFN-γ is an unexpected result. These four soluble factors are typically associated with a Th1 pro-inflammatory cytokine response, and glatiramer acetate is thought to act, in part, by dampening a Th1 response and promoting a Th2 response.

The precise mechanism of action of glatiramer acetate is complex and still not fully understood but the present methods provide a way to measure a sample copolymer preparation for activity, potency, stability, specificity (e.g., for equivalence to COPAXONE® or equivalence to a pharmaceutical specification range) of a test or candidate copolymer preparation.

What is claimed is:

1. A method for determining if a glatiramer acetate preparation is suitable for pharmaceutical use, the method comprising:
   (a) providing a myeloid cell;
   (b) contacting the myeloid cell with interferon-γ (IFN-γ) and a sample of a glatiramer acetate preparation;
   (c) measuring the production of at least one interferon-γ-induced protein selected from the group consisting of interferon-γ-inducible protein 10 (IP-10), interferon-inducible T cell α-chemoattractant (I-TAC), and monokine induced by interferon-γ (MIG) produced by the myeloid cell; and
   (d) comparing the production of at least one IFN-γ-induced protein produced by the myeloid cell to a reference value produced by a standardized batch of glatiramer acetate preparation and IFN-γ for the same at least one IFN-γ-induced protein; wherein if the production of said at least one IFN-γ-induced protein in (c) is 80-125% of the reference value, then the glatiramer acetate preparation is suitable for potential pharmaceutical use.

2. The method of claim 1, wherein step (b) comprises contacting the myeloid cell with a concentration of IFN-γ of between 0.01 ng/mL and 100 ng/mL, between 1 ng/mL and 50 ng/mL, or 10 ng/mL.

3. The method of claim 1, wherein the myeloid cell is a THP-I cell.

4. The method of claim 1, wherein the IFN-γ-induced protein is IP-10.

5. The method of claim 1 wherein the IFN-γ-induced protein is I-TAC.

6. The method of claim 1, wherein the IFN-γ-induced protein is MIG.

7. The method of claim 1, further comprising formulating at least a portion of the glatiramer acetate preparation for pharmaceutical use if the glatiramer acetate preparation is suitable for potential pharmaceutical use.

8. The method of claim 1, wherein the reference value is a cytokine induction profile, equivalence range or pharmaceutical specification for activity, potency, specificity or stability for a marketed pharmaceutical preparation of glatiramer acetate.

9. The method of claim 1, wherein step (b) comprises culturing the myeloid cell in the presence of the IFN-γ and the sample of a glatiramer acetate preparation for between 1 hour and 48 hours, between 6 hours and 36 hours, or between 12 hours and 24 hours.

10. The method of claim 1, wherein step (b) comprises contacting the myeloid cell with a concentration of the sample of the glatiramer acetate preparation of between 0.5 µg/mL and 100 µg/mL, contacting the myeloid cell with a concentration of the IFN-γ of between 1 ng/mL and 50 ng/mL, and culturing the myeloid cell in the presence of the IFN-γ and the sample of the glatiramer acetate preparation for between 12 hours and 24 hours, wherein the myeloid cell is a THP-I cell.

11. The method of claim 1, wherein the glatiramer acetate preparation is prepared by a method comprising: (i) polymerizing N-carboxy anhydrides of L-alanine, benzyl-protected L-glutamic acid, trifluoroacetic acid (TFA) protected L-lysine and L-tyrosine to generate a protected copolymer; (ii) treating the protected copolymer to partially depolymerize the protected copolymer and deprotect benzyl protected, (iii) deprotecting TFA-protected lysines to generate a glatiramer acetate preparation; and (iv) isolating the glatiramer acetate preparation.

* * * * *